United States Patent [19]

Zair

[11] Patent Number: 5,411,502

[45] Date of Patent: May 2, 1995

[54] SYSTEM FOR CAUSING ABLATION OF IRRADIATED MATERIAL OF LIVING TISSUE WHILE NOT CAUSING DAMAGE BELOW A PREDETERMINED DEPTH

[75] Inventor: Eliezer Zair, Bnei-Brak, Israel

[73] Assignee: Laser Industries, Ltd., Israel

[21] Appl. No.: 175,980

[22] Filed: Dec. 30, 1993

Related U.S. Application Data

[63] Continuation of Ser. No. 3,278, Jan. 12, 1993, abandoned.

[30] Foreign Application Priority Data

Jan. 15, 1992 [IL] Israel ......................................... 10664

[51] Int. Cl.⁶ .............................................. A61B 17/36
[52] U.S. Cl. .......................................... 606/10; 606/11
[58] Field of Search ........................... 606/9, 10, 11, 12

[56] References Cited

U.S. PATENT DOCUMENTS

| | | | |
|---|---|---|---|
| 3,884,236 | 5/1975 | Krasnov | 606/6 |
| 4,469,098 | 9/1984 | Davi | 606/7 |
| 4,566,453 | 1/1986 | Kumano et al. | 606/8 |
| 4,672,969 | 6/1987 | Dew | 606/3 |
| 4,917,083 | 4/1990 | Harrington et al. | 606/19 |
| 5,071,417 | 12/1991 | Sinofsky | 606/16 |

FOREIGN PATENT DOCUMENTS 0172490 2/1986 European Pat. Off. ............... 606/9

OTHER PUBLICATIONS

"Selective Photothermolysis: Precise Microsurgery by Selective Absorption of Pulsed Radiation" by Anderson and Parrish.

Primary Examiner—Stephen C. Pellegrino
Assistant Examiner—Sonya C. Harris
Attorney, Agent, or Firm—Cobrin, Gittes & Samuel

[57] ABSTRACT

A system for causing uniform ablation of irradiated material of living tissue while not causing damage below a predetermined depth where laser radiation is provided sequentially and continuously in a predetermined pattern is disclosed.

7 Claims, 5 Drawing Sheets

SYSTEM FOR CAUSING ABLATION OF IRRADIATED MATERIAL OF LIVING TISSUE WHILE NOT CAUSING DAMAGE BELOW A PREDETERMINED DEPTH

This is a continuation of application Ser. No. 003,278, filed Jan. 12, 1993, now abandoned.

FIELD AND BACKGROUND OF THE INVENTION

The present invention relates to a system for causing ablation of a target material of living tissue while not causing damage below a predetermined depth. The novel system is particularly useful using a carbon dioxide laser.

When using a laser for ablating tissue it is desirable to deliver maximum power density to the tissue to be ablated while minimizing temperature rise in adjacent tissue, particularly in the tissue underlying the tissue to be ablated preventing necrosis in such underlying tissue. Such a temperature rise in underlying tissue may cause thermal damage or carbonization, which generally results in increased scarring and healing time. For this purpose, surgical lasers used for tissue ablation are usually operated with short pulses to deliver high energy in short periods of time. Various pulsing techniques have been developed for this purpose, in which the energy applied for ablation is varied by changing the pulse repetition rate, pulse duration, and/or pulse energy.

Generally, it is desirable to provide power density of at least 40 watts/mm$^2$ in order to obtain ablation. This power density must be provided, however, for a short enough period of time so the ablation is without carbonisation, and to minimize thermal damage below a depth of 50 micrometers. At the same time, it is desirable to have a spot diameter on the tissue of at least 3 mm to allow for controllable ablation, since a smaller diameter is more likely to produce holes rather than uniform tissue removal. In the pulse technique for operating a laser, however, these desirable characteristics oppose each other.

In this regard it is generally desirable to expose the tissue to pulses of less than 1 msec to minimize the depth of thermal damage, and to provide at least 0.1 sec between pulses to allow the tissue to cool down, while at the same time to provide an average power of not less than 20–30 watts to reduce the surgery time. However, in the pulse technique for operating a laser, these desirable characteristics also oppose each other.

Various prior art techniques are known is which a target material is scanned with laser radiation to selectively cause necrosis of the target material. Such prior art uses lasers that are absorbed nonuniformally by the target material so as to cause the selective necrosis. One such prior art teaching is U.S. Pat. No. 4,733,660 which issued to Irving Itzkan on Mar. 29, 1988 and is entitled Laser System for Proving Target Specific Energy Deposition and Damage.

A second such prior art teaching is in an article entitled Hexascan: A New Robotized Scanning Laser Handpiece by D. H. McDaniel et al, which appeared in Volume 45 of CUTIS page 300 in May of 1990.

OBJECTS AND BRIEF SUMMARY OF THE INVENTION

An object of the present invention is to provide a novel laser system having advantages in the above respects when used for ablating a surface.

A system is provided for causing ablation of a target material of living tissue while not causing damage below a predetermined depth which includes a laser which generates a beam of laser radiation to be uniformly absorbed by the target material; a scanner for moving the beam of laser radiation in a predetermined pattern on the target material so that the "elements" of the target material are sequentially irradiated; and the rate at which the scanner moves the beam of laser radiation in the predetermined pattern is controlled so that ablation is caused uniformly on the target material but only to a predetermined depth.

In one embodiment of the system the scanning rate and predetermined pattern is such that each of the "elements" of the target material experiences a predetermined minimum time interval between applications of radiation thereto. In the preferred embodiment the predetermined minimum time interval is 0.1 seconds and the laser beam has an average power of at least 40 watts/mm$^2$.

In the preferred embodiment of this invention the scanner causes the beam of laser radiation to trace Lissajous figures over said target material.

In a further embodiment of this invention wherein the scanned laser beam defines a solid cone with a circular base projected onto the surface of said target material wherein the circular base projected onto the target material has a radius of at least 1.5 mm and the laser beam is focussed to a radius of no larger than 0.25 mm on the target material.

In the preferred embodiment of this invention the laser for generating the beam of laser radiation is a carbon dioxide laser.

BRIEF DESCRIPTION OF THE DRAWINGS

The invention is herein described, by way of example only, with reference to the accompanying drawings, wherein.

DESCRIPTION OF PREFERRED EMBODIMENTS

The Overall Method and System

Figure 1:
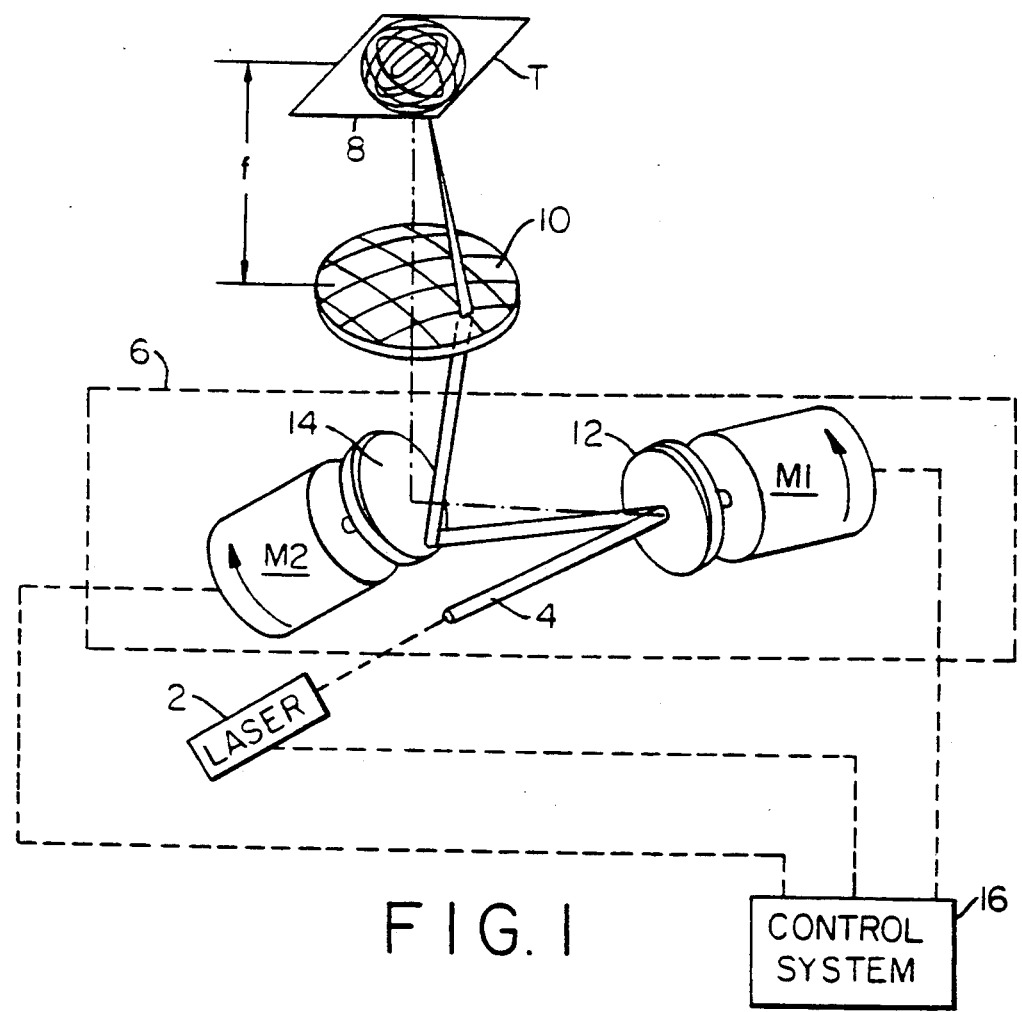
FIG. 1 illustrates one form of laser system constructed in accordance with the present invention.

FIG. 1 illustrates the main components of a laser system constructed in accordance with the present invention for use in ablating tissue, shown at T. Thus, the illustrated system includes a laser 2 which produces a continuous laser beam 4. In the preferred embodiment of this invention the laser 2 is a carbon dioxide laser. The continuous laser beam is applied to a laser scanner system, generally shown by box 6, which cyclically scans the beam along two orthogonal axes to cause the beam to trace Lissajous figures, shown generally at 8 in FIG. 1, over the tissue T to be ablated. The laser beam leaving the scanning system 6 first passes through a focussing lens 10 which focusses the laser beam on tissue T.

The scanning system 6 includes two mirrors 12, 14, each rotated by a motor $M_1$, $M_2$. These mirrors are so located with respect to the laser beam 4 and also to each other to cyclically scan the laser beam along two orthogonal axes, and to cause the beam to trace the Lissajous FIGS. 8 over the tissue T to be ablated.

Production of the Lissajous Figures

Figure 7:
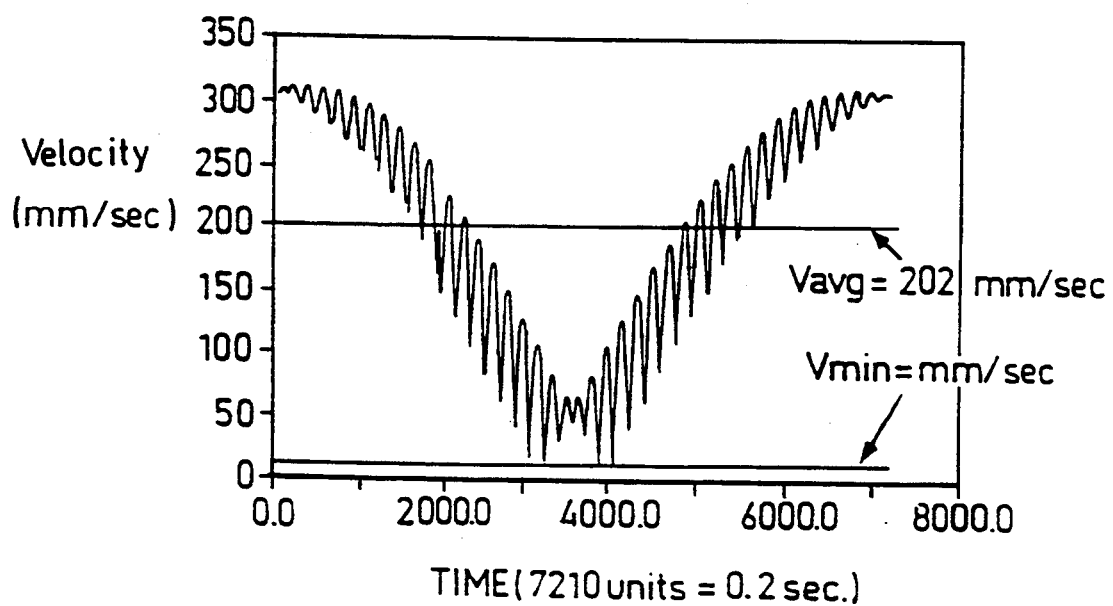
Figure 8:
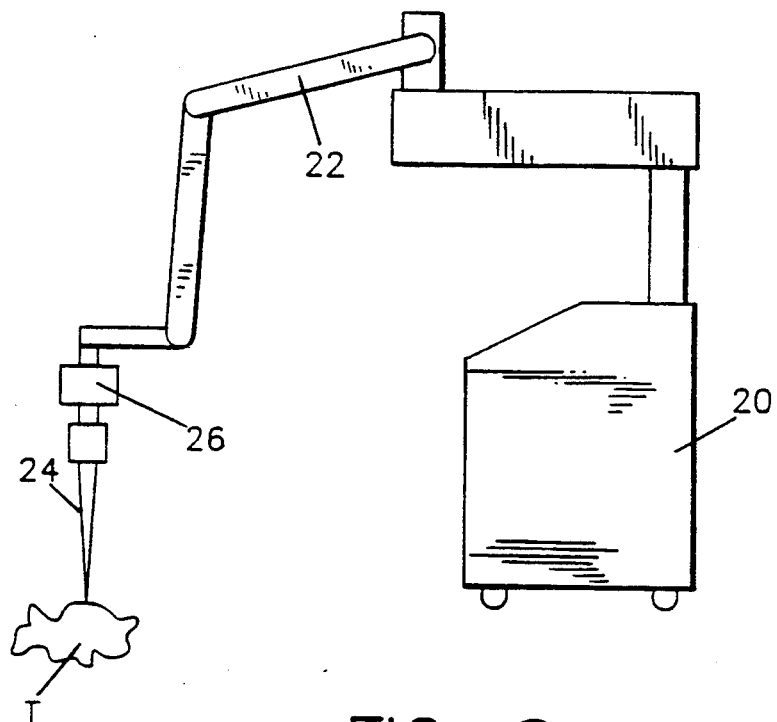
FIG. 8 illustrates a hand-held laser apparatus constructed in accordance with the present invention for use in free-hand surgery.

The manner in which the Lissajous FIGS. 8 are produced by the scanning mirrors 12, 14 will now be described particularly with reference to FIGS. 2–7.

Figure 2:
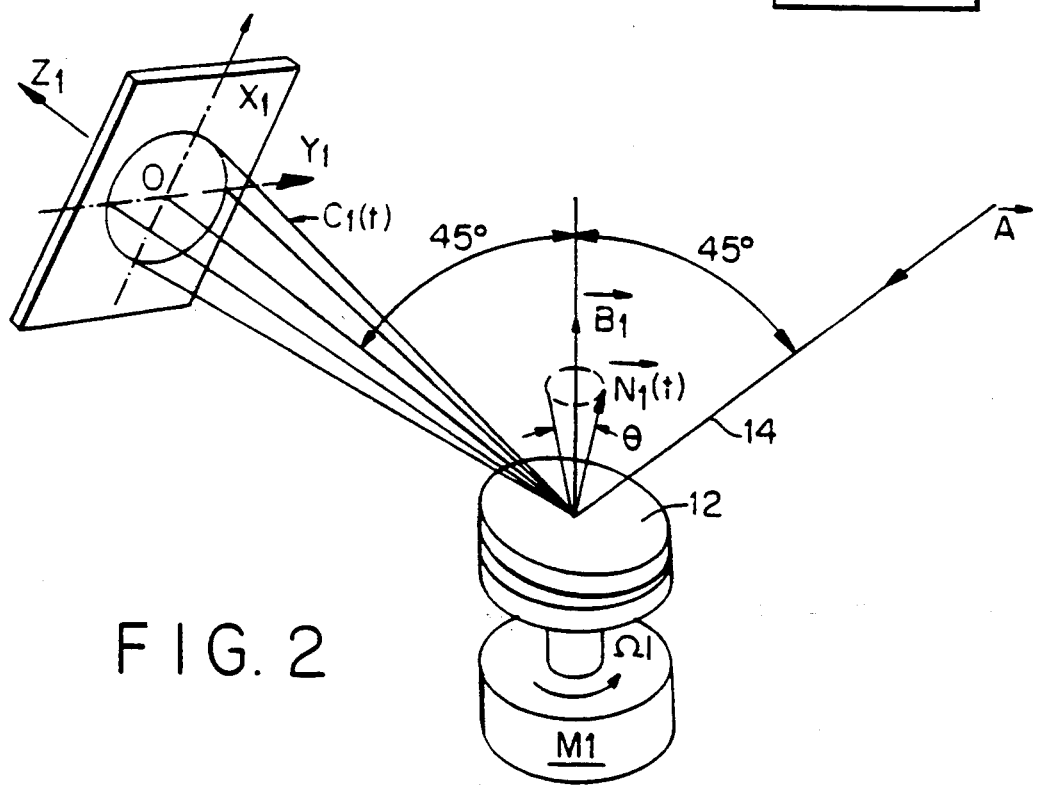
FIGS. 2–7 are diagrams helpful in explaining the Lissajous figures produced by the scanning system in the laser of FIG. 1.

FIG. 2 illustrates a system including motor M1 rotating at angular velocity $\Omega 1$ about an axis defined by the normalised vector B1. A mirror (e.g., 12, FIG. 1) is fixed to the motor such that its normal, defined by N1, lies at an angle of $\theta/2$ to the rotating axis B1. As the motor rotates, the vector N1 defines a cone of half angle $\theta/2$. The axis of symmetry of the cone is defined by the vector B1. A ray, defined by vector A, impinging on the mirror at an angle of 45° to axis B1 will, according to the laws of reflection, produce reflected rays described by the time dependent vector C1(t). This vector C1(t) traces an envelope of a cone with an elliptical base. The vector Z1, which represents the axis of this cone, lies in the plane defined by vectors A and B1. The angle between vectors Z1 and B1 is also 45 degrees.

A Cartesian coordinate system based on the three vectors X1, Y1 and Z1 may now be defined. The origin of this coordinate system is represented by $0_1$ in FIG. 2. The vector X1 lies in the plane containing vectors A, B1 and Z1, and is perpendicular to vector Z1. The direction of vector Y1 is perpendicular to vectors X1 and Z1.

The projections of the reflected rays can now be described by the following equations:

$$a_{x1}(t) = \Theta \cos (\Omega_1 t + \delta_1) \quad \text{Eq. 1}$$

$$a_{y1}(t) = \Theta/\sqrt{2} \sin (\Omega_1 t + \delta_1) \quad \text{Eq. 2}$$

where:

$a_{x1}(t)$ is the angle of the projection C1(t) in the plane X1-Z1;

$a_{y1}(t)$ is the angle of the projection of C1(t) on the plane Y1-Z1;

and $\delta 1$ is an arbitrary phase which defines the angles a at time t=0.

The relatively large displacement associated with amplitude $\Theta$ in equation (1) lies in the plane containing vectors A and B1. The smaller amplitude $\Theta/\sqrt{2}$ of equation (2) is in the direction of vector Y1.

Now can be added a second motor M2 (FIG. 3), whose axis is defined by vector B2 rotating with angular velocity $\Omega 2$. A mirror (e.g., 14, FIG. 1) whose normal is N2(t) is fixed to motor M2 forming an angle of $\Theta/2$ between normal N2(t) and vector B2 (as in motor M1). Motor M2 will be aligned such that the axis of vector B2 lies at 45° to the axis of vector Z1. Vector B2 also lies in the plane defined by vectors Z1 and Y1. As a result, there is obtained reflected rays C2(t) which form a solid cone with a circular (not elliptical) base. The axis of symmetry Z2 of this cone lies at 45° to the axis B1 of the motor M1 and in the plane defined by vectors Z2 and B2.

Figure 3:
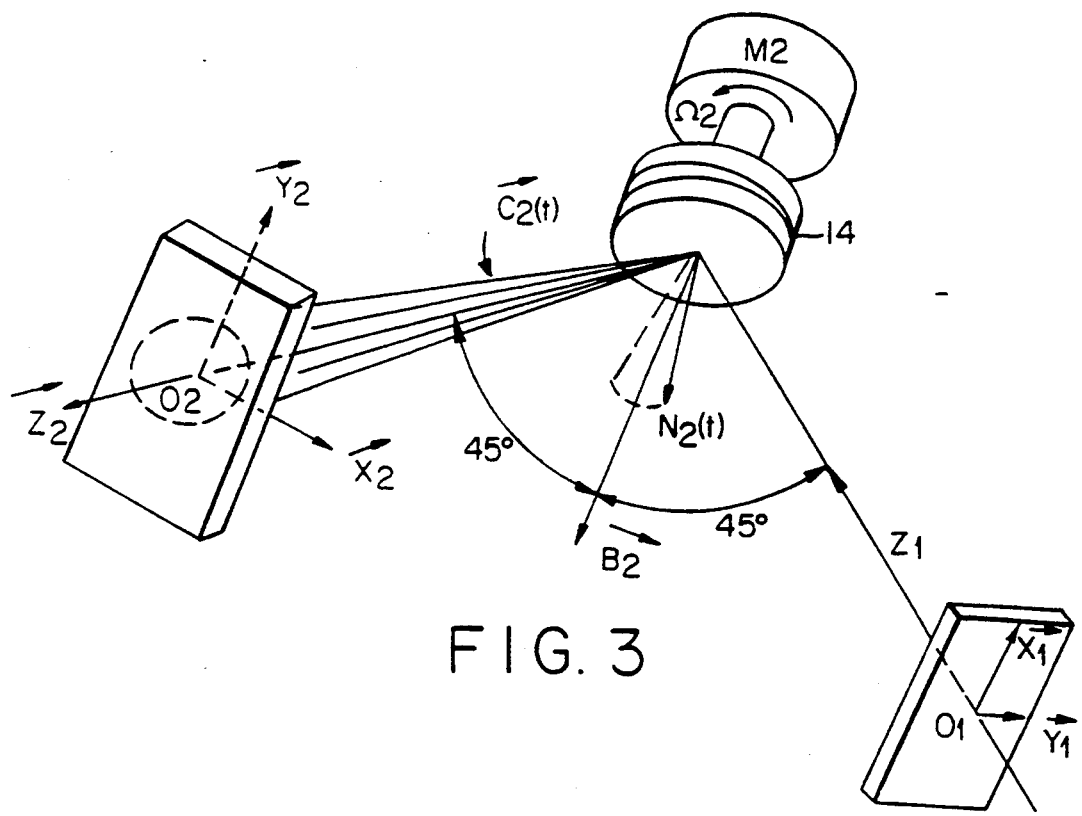

A new Cartesian coordinate system may now be defined having an origin at $0_2$ (see FIG. 3). Vector X2 is perpendicular to vector Z2 and lies in the plane defined by vectors B2 and Z2. Vector Y2 is perpendicular to vectors X2 and Z2.

The larger amplitude always exists in the X direction and the smaller amplitude in the Y direction. The two motors M1, M2 are aligned in such a way that the X direction of motor M1 combines with the Y direction of motor M2, and the Y direction of motor $M_1$ combines with the $-X$ direction of the second motor. In this way amplitude compensation is obtained, resulting in a cone with a circular (not elliptical) base.

All the rays C2(t) exiting from the second mirror (e.g., 14, in FIG. 1) are defined by the following equations:

$$a_{x2}(t) = -a_{y1}(t) + \theta\cos(\Omega 2 \cdot t + \delta 2) \quad \text{Eq. 3}$$
$$= -(\theta/\sqrt{2})\sin(\Omega \cdot t + \delta 1) + \theta\cos(\Omega 2 \cdot t + \delta 2)$$

$$a_{y2}(t) = \theta\sin(\Omega 1 \cdot t) + (\theta/\sqrt{2})\sin(\Omega_2 T + \delta 2) \quad \text{Eq. 4}$$
$$= \theta\cos(\Omega_1 t + \delta_1) + \theta/\sqrt{2} \sin(\Omega_2 t + \delta_2)$$

Assuming $\delta 1 = -90°$ and $\delta 2=0$ then:

$$a_{x2}(t) = (\Theta/\sqrt{2}) \cos (\Omega 1 \cdot t) + \Theta \cos(\Omega 2 t) \quad \text{Eq. 5}$$

$$a_{y2}(t) = \Theta \sin (\Omega 1 \cdot t) + (\Theta/\sqrt{2}) \sin (\Omega 2 \cdot t) \quad \text{Eq. 6}$$

The angle of the exiting rays formed with axis Z2 can exist between zero and $(\Theta + \Theta/\sqrt{2})$. Thus the rays fill the whole area of the base of the cone whose half angle is defined by $(\Theta + \Theta/\sqrt{2})$.

Figure 4:
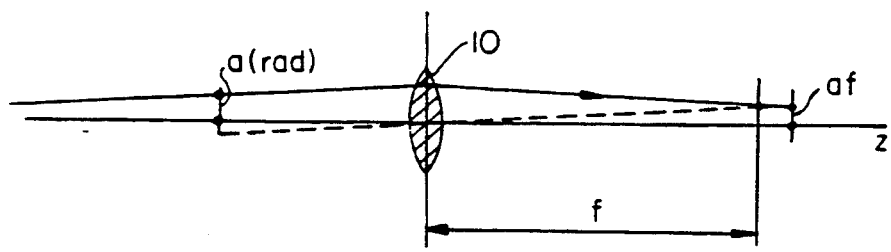
Figure 5:
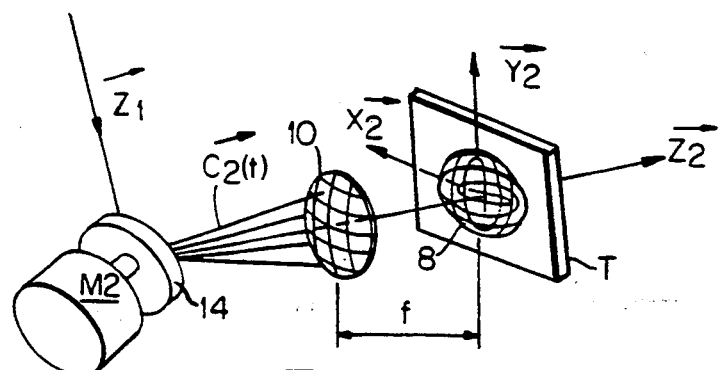
Figure 6:
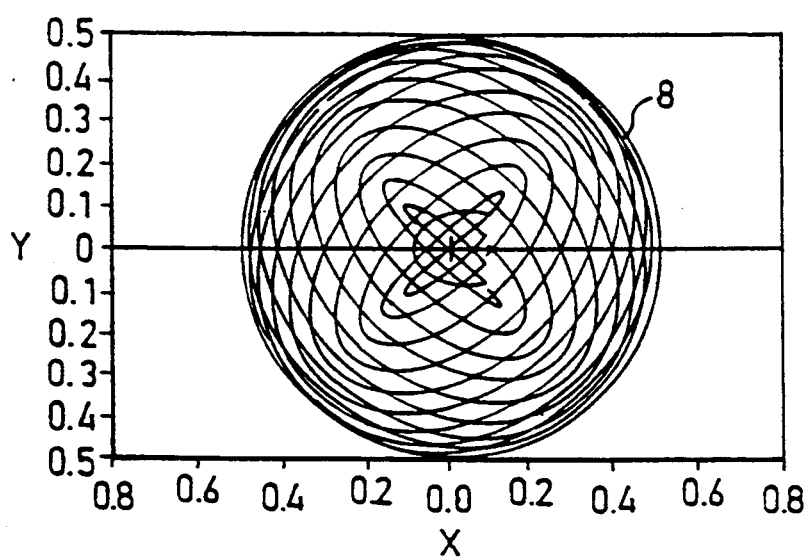

A ray which is focussed by a lens of focal length "f" (e.g., lens 10, FIG. 1), will be displaced at the back focal plane of the lens by an amount a.f, where a is the angle subtended by the ray and the optical axis of the lens (see FIG. 4).

If a lens is placed perpendicular to axis $Z_2$ (FIG. 5), a time dependent ray pattern will be produced at the focal plane of the lens (of focal length f), given by the following equations (see FIGS. 5 and 6):

$$x2(t) = f a_{x2(t)} = f(\Theta/\sqrt{2}) \cos (\Omega_1 {}^*t) + f\Theta \cos (\Omega_2 {}^*t) \quad \text{Eq. 7}$$

$$y2(t) = f a_{y2(t)} = f\Theta \sin (\Omega_1 {}^*t) + f(\Theta/\sqrt{2}) \sin (\Omega_2 {}^*t) \quad \text{Eq. 8}$$

For example, the lens may be of f=125 mm; the mirror wedge angle may be $\Theta = 2.34$ mRad; and the angular velocities may be $\Omega 1 = 600$ rad/sec and $\Omega 2 = 630$ rad/sec. Let $A = \Theta f/\sqrt{2} = 0.207$; $B = \Theta f = 0.293$; and $C = \Omega 2/\Omega 1 = 1.05$. The ray exiting from the lens will scan at the focal plane an area whose limits are defined by a circle of radius 0.5 mm (see FIG. 6). Every 20 revolutions the ray completely scans the whole area and starts anew. The 20 revolution scan period is about 0.2 seconds. The resultant ray pattern can be seen in FIG. 6.

Example of Laser for Free-Hand Surgery

FIG. 8 illustrates the invention in one form of laser apparatus used for free-hand surgery. The laser apparatus illustrated in FIG. 8, therein designated 20, outputs a laser beam via an articulated-arm system 22 and a handpiece 24 grasped by the surgeon for directing the laser beam to the appropriate locations of the tissue T to be ablated in accordance with the present invention, the laser of FIG. 8 includes a scanner system, generally designate 26, as described above for cyclically scanning the continuous laser beam along two orthogonal axes and thereby to cause the beam to trace Lissajous figures over the tissue T to be ablated. In the apparatus illustrated in FIG. 8, the focussing lens (10, FIG. 1) is in the hand-held handpiece gripped and manipulated by the surgeon.

Following is one example of the parameters of a hand laser apparatus such as illustrated in FIG. 8.
1. Lens focal length 125 mm
2. Scan Radius r=2.0 mm (A=0.828 mm, B=1.172 mm)
3. Laser Power P=20 watts
4. Raw Beam Radius (before lens) W1=4 mm
5. Rotation speed of motors
   $\Omega 1 = 600$ rad/sec
   $\Omega 2 = 630$ rad/sec
   $C = \Omega 2/\Omega 1 = 1.05$
6. Laser Wavelength  =0.0106 mm
7. From FIG. 7 we see that
   Vavg.=808 mm/sec
   Vmin.=44 mm/sec These two velocities, Vavg. and Vmin., are four times that shown in FIG. 7 because FIG. 7 represents a scan radius of 0.5 mm, whereas in the above example the radius is four times greater.

The above parameters produce the following results:
1. Spot radius at focus $$wO = \frac{f\lambda}{\pi W_1} = 0.1 \text{ mm}$$

2. Power density at focus P.D.=P/S=P/$\pi \cdot$w0$^2$=637 watts/mm' where S is the area of the focussed spot.

At this power density the thermal damage is minimal, and there are no signs of carbonisation. Assuming no scanning, the rate of evaporation Ve would be:

$$Ve = K \times P.D.$$
$$\text{where } K = 0.4 \text{ mm/joule}$$
$$\text{i.e. } Ve = 254.8 \text{ mm/sec.}$$

At such a large speed there is no way of controlling the homegeneity of tissue removal. As a result, deep holes and valleys are formed.

If the scanner is operated at a scan radius of r=2 mm, the average power density on the tissue within the scanning area is:

$$P/\pi \cdot r^2 = 20/\pi 19\ 4 = 1.6 \text{ watts/mm}^2$$

The rate of evaporation of the scanned area is:

$$Ve = KXP \cdot D. = 0.4 \times 1.6 = 0.64 \text{ mm/sec.}$$

At this speed it is easy to control the rate of tissue removal causing minimal damage.

Because of the scan speed, each element of the tissue feels the equivalent of a short time pulse. The pulse duration is given by the ratio of the spot diameter at the focus (2WO) to the linear scan speed (Vs) (see FIG. 7). The average pulse duration (Tavg.) is given by:

$$T\text{avg.} = 2WO/V\text{avg.} = 2 \times 0.1/808 = 250\ \mu\text{sec.}$$

Pulses of this duration give very low thermal damage. The time between successive pulses is 0.2 sec. This is the ideal time for the tissue to cool down. This is a further reason for low thermal damage.

Example of Laser for Microsurgery

Figure 9:
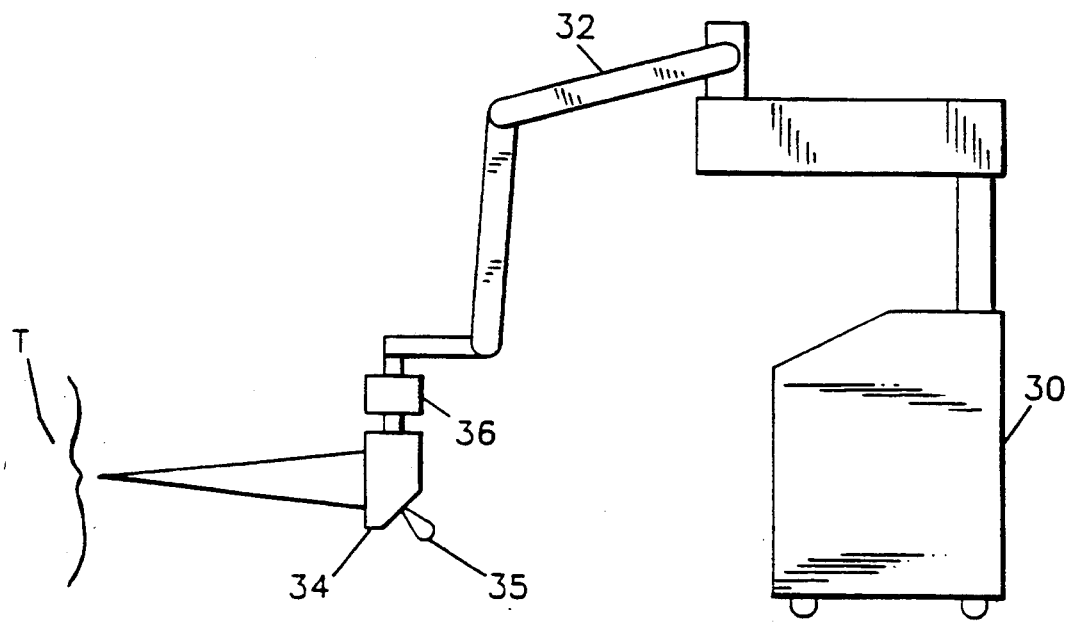
FIG. 9 illustrates another laser apparatus constructed in accordance with the present invention particularly useful for microsurgery.

FIG. 9 illustrates the invention included in another form of laser apparatus particularly useful for microsurgery. The laser, generally designated 30 in FIG. 9, outputs a laser beam via a system of articulated arms 32 and a micro-manipulator 34, such as described in U.S. Pat. No. 4,228,341, to the tissue T to be ablated. Micromanipulator 34 includes a joystick 35 enabling the surgeon to manipulate the laser beam as desired, and also an eyepiece and microscope (not shown) to permit the surgeon to view the working area containing the tissue to be ablated. The scanner system, generally designated 36, corresponds to the scanner system 6 in FIG. 1, and is effective to cyclically scan the continuous laser beam along two orthogonal axes as described above to cause the beam to trace Lissajous figures over the tissue to be ablated.

Following is one example of the parameters of a gynecological colposcope constructed as illustrated in FIG. 9 and having a working distance of 400 mm.
1. Focal length f=400 mm
2. Scan Radius r=2 mm
3. Laser Power 60 watts
4. Raw Beam radius w1=4 mm
5. Rotational speed of motors
   $\Omega 1 = 600$ rad/sec
   $\Omega 2 = 630$ rad/sec
6. Laser wavelength  =0.0106 mm
7. From FIG. 8
   Vavg.=808 mm/sec
   Vmin.=44 mm/sec The laser apparatus illustrated in FIG. 9 and constructed in accordance with the foregoing parameters produces the following results:

$$wO = \frac{f\lambda}{\pi W_1} = 0.34 \text{ mm}$$

2. Power Density at focus P.D.=P/S=P/$\pi$wO$^2$=165 watts/mm$^2$.

At this power density the thermal damage and carbonisation is minimal.

3. Assuming no scanning, the rate of evaporation would be:

$$Ve = 0.4 \times P.D. = 0.4 \times 165 = 66 \text{ mm/sec}$$

This represents a speed too great for controlled work. With the scanner, P.D.=P/$\pi$r$^2$=60/$\pi$2$^2$=4.78 watts/mm$^2$, and the rate of evaporation Ve=0.4$\times$P.D.=0.4$\times$4.78=1.9 mm.sec. This represents an evaporation rate which is very convenient for efficient working conditions.

4. Pulse duration Tavg=2Wo/Vavg=2$\times$0.34/808=840 $\mu$sec.

Pulses of this duration create very low thermal damage.

While the invention has been described with respect to several preferred embodiments, it will be appreciated that these are set forth merely for purposes of example, and that many variations may be made. For example, the scanning need not trace Lissajous figures; in fact, only one scanning mirror is needed since the movement of the laser by the surgeon will cause the beam to scan the surface to be ablated. Also, more than two mirrors could be used. Many other variations, modifications and applications of the invention may be made.

What is claimed:

1. A system for causing ablation of an irradiated material of living tissue while not causing necrosis below a predetermined depth, said irradiated material consisting of a plurality of elements; said system including:
   means for generating a beam of laser radiation to be uniformly absorbed by said irradiated material;
   a scanner means for moving said beam of laser radiation in a predetermined pattern on said irradiated material so that said elements of said irradiated material are sequentially and continuously irradiated; and
   means for controlling the scanner means to move said beam of laser radiation in said predetermined pattern so that ablation of said irradiated material of living tissue is caused uniformly but only to a predetermined depth.

2. The system according to claim 1, wherein each of said elements of said irradiated material experiences a predetermined minimum time interval between applications of radiation thereto.

3. The system as defined in claim 2 in which said predetermined minimum time interval is 0.1 of a second.

4. The system as defined in claim 3 wherein the laser beam has an average power density of at least 40 watts/mm$^2$.

5. The system according to any one of claims 1-4, wherein the scanner causes the beam of laser radiation to trace Lissajous figures over said irradiated material.

6. The system according to any one of claims 1-4 in which said means for generating a beam of laser radiation is a carbon dioxide laser.

7. The system as defined in claim 5 in which said means for generating a beam of laser radiation is a carbon dioxide laser.

* * * * *